United States Patent
Sakai et al.

(10) Patent No.: US 7,521,079 B2
(45) Date of Patent: Apr. 21, 2009

(54) **PROCESS FOR PRODUCING AN EXTRACT OF *HYDRANGEA* CONTAINING PLANT POWDER**

(75) Inventors: Yasushi Sakai, Tsukuba (JP); Yoshiharu Yokoo, Sagamihara (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 858 days.

(21) Appl. No.: 10/481,519

(22) PCT Filed: Jun. 21, 2002

(86) PCT No.: PCT/JP02/06226

§ 371 (c)(1),
(2), (4) Date: Dec. 19, 2003

(87) PCT Pub. No.: WO03/000074

PCT Pub. Date: Mar. 1, 2003

(65) Prior Publication Data

US 2004/0161524 A1   Aug. 19, 2004

(30) Foreign Application Priority Data

Jun. 21, 2001   (JP) .............................. 2001-188480

(51) Int. Cl.
*A23L 1/28* (2006.01)

(52) U.S. Cl. ........................ 426/655; 426/594; 426/597; 426/433

(58) Field of Classification Search .................. 426/597, 426/433, 594

See application file for complete search history.

(56) References Cited

U.S. PATENT DOCUMENTS

| | | | | |
|---|---|---|---|---|
| 4,063,994 | A | * | 12/1977 | Gasser et al. .................. 159/49 |
| 4,281,023 | A | * | 7/1981 | Pyves .......................... 426/385 |
| 4,512,983 | A | * | 4/1985 | Shino et al. ............. 424/195.15 |
| 4,808,409 | A | * | 2/1989 | Kinghorn et al. ............. 424/439 |

FOREIGN PATENT DOCUMENTS

| | | | |
|---|---|---|---|
| JP | 53-59075 | * | 5/1978 |
| JP | 60-43338 | * | 3/1985 |
| JP | 01-262772 | | 1/1989 |
| JP | 2-131543 | * | 5/1990 |
| JP | 03-103143 | | 4/1991 |
| JP | 5-336939 | * | 12/1993 |
| JP | 11-056277 | | 3/1999 |
| WO | WO 97/05888 | | 2/1997 |

* cited by examiner

*Primary Examiner*—Anthony Weier
(74) *Attorney, Agent, or Firm*—Fitzpatrick, Cella, Harper & Scinto

(57) ABSTRACT

The present invention relates to a method for producing a liquid plant extract containing plant powder, which includes concentrating a liquid extract containing an active ingredient in the presence of the plant powder, the liquid extract being obtained from a plant containing the active ingredient; a process for producing a plant extract containing plant powder, which is characterized by concentrating and drying a liquid extract containing an active ingredient in the presence of the plant powder.

16 Claims, No Drawings

PROCESS FOR PRODUCING AN EXTRACT OF *HYDRANGEA* CONTAINING PLANT POWDER

TECHNICAL FIELD

The present invention relates to a method for extracting and condensing an active ingredient from a plant containing the active ingredient, a liquid extract or plant extract containing the active ingredient, and a food and drink or feed which comprises the liquid extract or plant extract.

BACKGROUND ART

Extraction of a plant containing an active ingredient, for example, Hydrangeae Dulcis Folium, which can be prepared by collecting and fermenting the leaves and branches of *Hydrangea macrophylla* SERINGE var. *Thunbergii Makino* followed by drying, with various solvents such as a mixture of a fat-soluble organic solvent and water affords a liquid extract containing an active ingredient such as phyllodulcin. The concentrated liquid extract, however, yields highly viscous taffy-like precipitate.

The taffy-like precipitate tends to stick to the bottom of a vessel or block a pipeline, and it is difficult to transfer to another vessel.

On the other hand, the liquid extract containing an active ingredient obtained by extraction with a solvent such as ethanol, when dried by direct drying with a spray-drier or with drum drier through no procedure for concentration, affords a very low recovery because the content of the solid component in the liquid extract is low. In addition, this operation is not a practical way because it requires special equipment such as explosion protector.

Therefore, it is difficult to produce powder highly containing an active ingredient on an industrial scale using a spray-drier or freeze drier.

On the other hand, the taffy-like precipitate is not suitable for use in foods and drinks or feeds or as raw material thereof because the directly dried precipitate is very hard.

The extract of Hydrangeae Dulcis Folium with supercritical carbon dioxide or liquidized carbon dioxide is rich in phyllodulcin as an ethanol-soluble sweetening component, which is however not easy to handle because it is in a form of paste (Japanese Published Unexamined Patent Application No. 262772/89).

As plant powder, Hydrangeae Dulcis Folium powder is exemplified, but the content of phyllodulcin in the powder is as low as 1 to 2% by weight because it is prepared by pulverizing Hydrangeae Dulcis Folium as such. Though the commercially available powder of Hydrangeae Dulcis Folium extract for use in foods and drinks is prepared by extraction of Hydrangeae Dulcis Folium with a water-soluble solvent, the content of phyllodulcin is as low as 2% by weight or less.

Thus, it is not possible to increase the content of an active ingredient in the plant powder by merely pulverizing the plant.

DISCLOSURE OF INVENTION

An object of the present invention is to provide a process for extracting an active ingredient from a plant containing the active ingredient, a liquid extract or plant extract containing the active ingredient, and a food and drink or feed comprising the liquid extract or plant extract.

The invention of the present application relates to the following items (1) to (38).

(1) A process for producing a liquid plant extract containing plant powder, which comprises: concentrating a liquid extract containing an active ingredient in the presence of the plant powder, the extract being obtained from the plant containing the active ingredient.

(2) A process for producing a liquid plant extract containing plant powder, which comprises a step of preparing a liquid extract containing an active ingredient from a plant containing the active ingredient, and a step of concentrating the liquid extract in the presence of plant powder.

(3) A process for producing a plant extract containing plant powder, which comprises concentrating and drying a liquid extract containing an active ingredient in the presence of plant powder and said liquid extract being obtained from the plant containing the active ingredient.

(4) A process for producing a plant extract containing plant powder, which comprises a step of preparing a liquid extract containing an active ingredient from a plant containing the active ingredient, a step of concentrating the liquid extract in the presence of plant powder to give a liquid plant extract containing the plant powder, and a step of drying the liquid plant extract containing the plant powder.

(5) A process as described in any of the items (1) to (4), wherein the liquid extract containing an active ingredient is prepared by extracting the plant containing the active ingredient with aqueous ethanol and removing the resultant plant residue.

(6) A process as described in any of the items (1) to (5), wherein the plant powder is present in an amount of 19 to 1/19 parts by dry weight based on 1 part of the liquid extract containing the active ingredient by dry weight.

(7) A process as described in any of the items (1) to (6), wherein the plant containing an active ingredient is a plant belonging to the genus *Hydrangea*.

(8) A process as described in any of the items (1) to (6), wherein the plant containing an active ingredient is *Hydrangea macrophylla* SERINGE var. *Thunbergii Makino*.

(9) A process as described in any of the items (1) to (8), wherein the active ingredient is an ethanol-soluble one.

(10) A process as described in any of the items (1) to (8), wherein the active ingredient is phyllodulcin.

(11) A process as described in any of the items (1) to (10), wherein the plant powder is in the form of particles of 0.1 μm to 1 mm in average particle size in dry state.

(12) A process as described in any of the items (1) to (11), wherein the plant powder is a plant belonging to the genus *Hydrangea*.

(13) A process as described in any of the items (1) to (11), wherein the plant powder is Hydrangeae Dulcis Folium powder, green tea powder or turmeric powder.

(14) A process as described in any of the items (1) to (13), wherein the concentration is conducted by heating under reduced pressure.

(15) A process as described in any of the items (3) to (14), wherein the method of drying is freeze-drying or heating under reduced pressure.

(16) A liquid plant extract containing plant powder which comprises a liquid extract containing an active ingredient obtained from a plant containing the active ingredient and comprises a plant powder, wherein the content of the active ingredient in the liquid extract is higher than that in the plant.

(17) A liquid plant extract containing plant powder as described in the item (16), wherein the liquid extract containing the active ingredient is prepared by extraction with aqueous ethanol.

(18) A liquid plant extract containing plant powder as described in the item (16) or (17), which comprises the plant powder in an amount of 19 to 1/19 parts by dry weight based on 1 part of the liquid extract containing the active ingredient by dry weight.

(19) A liquid plant extract containing plant powder as described in any of the items (16) to (18), wherein the plant containing an active ingredient is a plant belonging to the genus *Hydrangea*.

(20) A liquid plant extract containing plant powder as described in any of the items (16) to (18), wherein the plant containing an active ingredient is *Hydrangea macrophylla* SERINGE var. *Thunbergii Makino*.

(21) A liquid plant extract containing plant powder as described in any of the items (16) to (20), wherein the active ingredient is an ethanol-soluble one.

(22) A liquid plant extract containing plant powder as described in any of the items (16) to (20), wherein the active ingredient is phyllodulcin.

(23) A liquid plant extract containing plant powder as described in any of the items (16) to (22), wherein the plant powder is in the form of particles of 0.1 µm to 1 mm in average particle size in dry state.

(24) A liquid plant extract containing plant powder as described in any of the items (16) to (23), wherein the plant powder is a plant belonging to the genus *Hydrangea*.

(25) A liquid plant extract containing plant powder as described in any of the items (16) to (23), wherein the plant powder is Hydrangeae Dulcis Folium powder, green tea powder or turmeric powder.

(26) A plant extract containing plant powder which comprises an extract containing an active ingredient obtained from a plant containing the active ingredient and comprises a plant powder, wherein the content of the active ingredient in the extract is higher than that in the plant.

(27) A plant extract containing plant powder as described in the item (26), wherein the extract containing an active ingredient is prepared by extraction with aqueous ethanol.

(28) A plant extract containing plant powder as described in the item (26) or (27), which comprises the plant powder in an amount of 19 to 1/19 parts by dry weight based on 1 part of the extract containing the active ingredient by dry weight.

(29) A plant extract containing plant powder as described in any of the items (26) to (28), wherein the plant containing an active ingredient is a plant belonging to the genus *Hydrangea*.

(30) A plant extract containing plant powder as described in any of the items (26) to (28), wherein the plant containing an active ingredient is *Hydrangea macrophylla* SERINGE var. *Thunbergii Makino*.

(31) A plant extract containing plant powder as described in any of the items (26) to (30), wherein the active ingredient is an ethanol-soluble one.

(32) A plant extract containing plant powder as described in any of the items (26) to (30), wherein the active ingredient is phyllodulcin.

(33) A plant extract containing plant powder as described in any of the items (26) to (31), wherein the plant powder is in the form of particles of 0.1 µm to 1 mm in average particle size in dry state.

(34) A plant extract containing plant powder as described in any of the items (26) to (33), wherein the plant powder is that of a plant belonging to the genus *Hydrangea*.

(35) A plant extract containing plant powder as described in any of the items (26) to (33), wherein the plant powder is Hydrangeae Dulcis Folium powder, green tea powder or turmeric powder.

(36) A plant extract containing plant powder as described in any of the items (26) to (35), which is in the form of powder.

(37) A food and drink or feed comprising as an additive a liquid plant extract containing the plant powder as described in any of the items (16) to (25).

(38) A food and drink or feed comprising as an additive a plant extract containing the plant powder as described in any of the items (26) to (36).

BEST MODE FOR CARRYING OUT THE INVENTION

As the plant containing an active ingredient, any plant may be used as far as it contains the active ingredient, for example, wild plant, cultivated plant, or plant obtained by tissue culture.

The term "plant" includes leaves, flowers, branches, stems, fruits, roots, seeds, cultured cells or organs, or callus, which are used as such or after being treated physically, chemically or biologically.

The physical or chemical treatment includes drying such as sun-drying, air-drying, freeze-drying, disruption, and extraction. The physically or chemically treated matters include dried matters, freeze-dried matters, disrupted matters and extracted matters.

The biological treatment includes fermentation and the biologically treated matters include fermented products.

The term "plant containing an active ingredient" includes those as described in Notification No. 243 issued by Director General of Pharmaceutical Bureau, the Ministry of Health, Labor and Welfare, "On Revision of the Criterion for the Scope of Pharmaceuticals", Attachment 3, "List of Component Essence (Raw Materials) Recognized as Foods as far as their indication as pharmaceuticals is not advocated"; those as described in Notification No. 243 issued by Director General of Pharmaceutical Bureau, the Ministry of Health, Labor and Welfare, "On Revision of the Criterion for the Scope of Pharmaceuticals", Attachment 2, "List of Component Essence (Raw Materials) Used Exclusively as Pharmaceuticals"; and those belonging to the genus *Hydrangea*, among which a plant of *Hydrangea* is preferably used.

The plants described in Notification No. 243 issued by Director General of Pharmaceutical Bureau, the Ministry of Health, Labor and Welfare, "On Revision of the Criterion for the Scope of Pharmaceuticals", Attachment 3, "List of Component Essence (Raw Materials) Recognized as Foods as far as their indication as pharmaceuticals is not advocated" include *Chondrus crispus*, *Euphrasia officinalis*, phoenix tree, sisal hemp, goose foot, *Astilbe thunbergii*, *Trifolium pratense*, akatetsu, *Ulmus fulva*, common pyrethrum, *Mallotus japonicus*, *Salidago virga-aurea* var. *asiatica*, *Akebia quinata*, *Cannabis sativa*, *Pharbitis nil*, *Allium schoenoprasum* var. *foliosum*, *Phragmites communis*, *Hydrangea macrophylla*, *Angelica keiskei*, *Phaselus angularis*, *Thujopsis dolabrata*, *Malpighia glabra*, akkeshisou, burnet-saxifrage, afanizomezon, avocadao, flax, *Hydrangea macrophylla* subsp. *serrata* var. *thunbergii*, *Gynostemma pentaphyllum*, *Tulipa edulis*, *Zanthoxylum americanum*, American ginseng, *Apios americana*, aragao, *Acacia senegal*, arame, *Chenopodium ambrosioides*, marsh mallow, alfalfa, aloe, angelica, kidney vetch, *Prunus japonica*, *Polygonatum odoratum* var. *pluriflorum*, *Plumbago zeylanicum*, *Polygonum cuspidatum*, *Taxus cuspidate*, fig tree, *Abutilon avicennae*, *Ginkgo biloba*, carob, *Evodia danielli*, *Draba nemorosa*, *Veronica didyma* var. *lilacina*, *Nepeta cataria*, *Salanum nigrum*, *Oryza sativa*, *Thymus quinguecostatus*, *Tinospora crispa*, *Urtica thunbergiana*, *Clematis chinensis*, *Conandron ramondioides*, *Ixeris stolonifera*, *Rhodiola rosea*, *Dolichos lablab*, *Cissus sicyoides*, Indian amacha, Indian karatachi, *Piper longum*, Indian yakouboku, inpethiginosa, inperatoria, fennel, *Withania somnifera*, *Scrpus fluviatilis* var. *yagara*, *Acanthopanax sieboldianus*, tumeric, *Lindera umbellate*, tree marrow, *Opuntia ficus-indica*, *Licuala grandis*, *Aralia cordata*, *Stauntonia hexaphylla*, *Ranunculus japonicus*, Japanese apricot, *Chimaphila japonica*, *Lindera strychnifolia*, *Quercus salicina*, *Prunus grayana*, *Echinacea angustifolia*, *Artemisia drucunculus*, *Acanthopanax senticosus*, ezochichikogusa, *Fragaria vesca*, *Cytisus scoprius*, *Flammulina velutipes*, *Cassia obtusifolia*, enshuushou, *Sophora japonica*, *Avena sativa*, *Embelia ribes*, *Isodon japonicus*, *Astragalus membranaceus*, *Scutellaria baicalensis*, oushuuhannoki, *Polygonatum sibiricum*, *Phellodendron amurense*, *Dioscorea bulbifera forma spontanea*, *Coptis japonica*, *Ficus pumila*, *Plantago asiatica*, oohangousou, oohireazami, *Hordeum vulgare*, *Senecio integrifolius* var. *spathuatus*, *Salsola komarovi*, *Panax ginseng*, *Hypericum erectum*, otomeazea, *Lamium album* var. *barbatum*, gorgon plant, operukurinatarupetamu, *Olea europeaea*, *Sargassum pallidum*, sea onion, *Allium bakeri*, *Pueraria Mirifica*, *Diospyros kaki*, *Juglans regia* var. *orientis*, black currant, zedoary, kashutou, kathaba, *Valeriana fauriei*, *Typha latifolia*, kabanoanatake, kahun, pumpkin, *Typha latifolia*, German chamomile, *Myrciaria dubia*, *Cyperus microiria*, *Vicia satira*, oat fiber, guarana, kariusuforesukorii, karukehha, *Tamarindus inidica*, goat's rue, *Trichosanthes kirilowii* var. *japonica*, *Coriolus versicolor*, *Prunus armeniaca* var. *ansu*, sugar cane, *Glycyrrhiza uralensis*, kanbui, *Camptotheca acuminata*, rubus, *Platycodon grandiflorum*, *Hovenia dulcis*, *Helianthus tuberosus*, *Chrysanthemum morifolium*, *Cichorium intybus*, *Auricularia auricula*, *Citrus junos*, *Aloe arborescens*, *Ludwigia octovalvis* var. *sessiliflora*, *Satureja hortensis*, *Dictyophora indusiata*, *Chenopodium quinoa*, blessed thistle, *Anoectochilus formosanus*, *Rumex nepalensis*, *Gymnema sylvestre*, *Manihot esculenta*, *Uncaria tomentosa*, kyuusetsucha, gyuu-hakutou, *Allium victorialis* var. *platyphyllum*, rose bay, *Tamarix chinensis*, *Calluna vulgaris*, *Ajuga decumbens*, kirinsou, *Fortunella japonica* var. *margarita*, *Lonicera japonica*, *Hypericum patulum*, *Hemerocallis fulva* var. *kwanso*, *Desmodium styracifolium*, kinsenren, *Leucaena leucocephala*, *Piper betle*, *Agrimonia pilosa*, *Osmanthus fragrans* var. *aurantiacus*, *Tropaeolum majus*, guako, common guava, guaiacum, absinthium, *Lycium chinense*, *Chaenomeles japonica*, *Corydalis bungeana*, *Pueraria lobata*, *Cinnamomum camphora*, *Sasa veitchii*, *Verbena officinalis*, *Berchemia racemosa*, cat whiskers, *Cuminum cyminum*, kurachai, cranberry, Greenland isotsutsuji, *Asperula odorata*, grapefruit, clove tree, black mustard, black walnut, *Ribes nigrum*, kuromai, *Pongamia pinnata*, *Chlorella vulgalis*, *Morus bombycis*, *Veronica undulata*, *Millettia reticulata*, keikotusou, cinnamon bark, kale, poppy, *Epiphyllum oxpetalum*, laurel, kelp, ken, *Combretum grandiflorum*, gentian, brown rice germ, sekiren, *Engelhardtia chrysolepis*, *Elsholtzia ciliata*, *Pinguicula ramosa*, red algae, *Nuphar japonicum*, coffee, cola, *Acan-thopanax sessiliflorus*, *Vaccinium vitis-idaea*, *Euphrasis insignis* subsp. *iinumai*, pepper, kojin, coriander, *Bidens pilosa*, *Lysimachia japonica*, *Elfvingia applanata*, burdock, sesame, *Pyhllanthus urinaria*, wheat, *Ficus elastica*, rice starch, koribi, *Averrhoa carambola*, fenugreek, *Laminaria japonica*, comfrey, *Hippophae rhamnoides*, *Gleditshia japonica*, bupleurum root, asiasarum root, *Cremastra appendiculata*, sakyou, *Primula sieboldi*, *Punica granatum*, sago palm, *Sassafras albidum*, sugar beet, saffron, *Saponaria officinalis*, salacia, *Salacia oblonga*, *Smilax china*, *Actinidia arguta*, salvia, sankakutou, *Smilax Rhizome*, *Crataegus cuneata*, pansy, gardenia fruit, *Panax pseudo-ginseng*, cornus fruit, zanthoxylum fruit, *Rosa hirtula* var. *hirtula*, zizyphi spinosi semen, kaempferia, *Cassia nomama*, dioscorea rhizome, *Butyrospermum parkii*, *Lentinula edodes*, *Quisqualis indica*, sikeijyotei, *Lawsonia inermis*, *Eleusine coracana*, jijin, perilla, *Betula pendula*, *Pterocarpus santalinus*, violaceae, *Tilia japonica*, *Elymus repens*, *Kochia scoparia* var. *littorea*, *Pandanus veitchii*, *Capsicum frutescens*, shaupedekouro, shaenshi, *Stellaria alsine* var. *undulata*, peony root, *Adenophora tripylla* var. *japonica*, jasmine, jatoba, jabyakushi, *Piper retrofractum*, houttuyia herb, jurubeba, *Trachycarpus fortunei*, ginger, cardamon, *Isatis tinctoria*, *Rheum rhabarbarum*, pruinosa, *Betula platyphylla sukatchev* var. *japonica*, *Bletilla striata*, *Rosa roxburgii* var. *plena*, *Tremella fuciformis*, *Myrica cerifera*, *Lycopodium clavatum*, shintokukusunoki, sweet orange, zuikaku, sorrel, skullcap, horsetail, *Ribes sinanense*, stevia, *Pinus strobus*, spirulina, spearmint, *Pfaffia glomerata*, dividivi, violet, surimuamaransu, zurukamara, *Cyclocarya paliurus*, seitaka-kanabikisou, beleric myrobalan, *Citrus tangerina*, *Rubia tinctorum*, *Urtica dioica*, *Melilotus officinalis*, St. John's wort, *Rubus idaeus*, *Agrimonia eupatoria*, *Primula obconica*, *Crataegus oxyacantha*, *Tilia xeuropium*, white willow, prune, *Taraxacum officinale*, horse chestnut, *Fraxinus excelsior*, meadow sweet, elder, chaste berry, juniper, yarrow, peppermint, *Ilex aguifolium*, *Vaccunium myrtillus*, mushroom, *Prunus avium*, barberry, sekikoujyu, *Acorus gramineus*, *Vallisneria natans*, *Alnus japonica*, *Sambucus sieboldiana*, setsurenka, common mallow, *Thymus serpyllum*, celery, cnidium rhizome, *Dioscorea nipponica*, *Andrographis paniculata*, sensou, sensoutou, *Melia azedarach* var. *subtripinnata*, senna leaf, *Curculigo orchioides*, *Senecio scandens*, *Thuja orientalis*, buckwheat, Chinese anise, rhubarb, daikettou, *Geum japonicum*, *Pseudosteiiar mheterophylia*, soybean, jujube, taiwansuku, *Trachelospermum jasminoides*, *Bidens tripartita*, *Blumea balsamifera*, *Eclipta prostrate*, Bombay black wood, bamboo, hollyhock, thyme, *Citrus tachibana*, Brazilian cherry, Tartary buckwheat, *Polygonum tinctorium*, taheebo, tamogidake, *Aralia elata*, *Ilex latifolia*, *Salvia multiorhiza*, *Lophatherum gracile*, tanteihihou, chia, *Sasa kurilensis*, chishimarurisou, tea, chervil, cha de bugre, *Passiflora incarnata*, *Uncaria rynchophylla*, clove, globe artichoke, citrus unshiu peel, *Galeola septentronalis*, *Evernia prunastri*, camellia, *Centella asiatica*, *Commelina communis* var. *communis*, tsuriganedake, *Pleuropterus mutiflorus*, *Tetragonia tetragonoides*, *Codonopsis lanceolata*, *Basella rubra*, tilleul, devil's claw, dunaliella, *Gelidium amansii*, *Rubus suauissmus*, *Asparagus cochinchinensis* var. *cochinchinensis*, *Beninucasae semen*, *Capsicum annuum*, *Abutili semen*, marigold, *Cordycips sinensis*, corn, *Chelidonium majus* var. *asiaticum*, *Centipeda minima*, *Passiflora caerulea*, *Juniperus rigida*, *Aesculus turbinate*, *Eucommia ulmoides*, dog rose, tomato, tongkat ali, *Ruscus aculeatus*, *Capsella bursa-pastoris*, *Chrysanthemum parthenium*, natto, *Phoenix dactylifera*, *Sorbus commixta* var. *commixta*, gerangal, *Choerospondias axillaris* var. *japonica*, nanshouya-maimo, *Jatropha curcas*, sweet violet, *Momordica charantia*, nutmeg, *Euonymus alatus* var. *alatus*, *Tithonia diversifolia*, *Ligustrum japonicum*, scallion, *Ulmus americana*, ginseng, *Vitex cannabifolia*, garlic, *Cuphea carthagenensis*, *Albizzia julibrissin*, *Celosia argentea*, *Sonchus oleraceus*, saw palmetto, *Ampelopsis glandulosa* var. *heterophylla*, wild betal, pineapple, hibiscus, pau d' arco, malt, hakucha, hakutousugi, hakuhishou, stitchwort, *Achillea sibirica*, *Portulacea oleracea*, *Musa basjoo*, *Nelumbo nucifera*, parsley, butternut, pata de vaca, *Mentha arvensis*, hakkakureishi, huckleberry, *Mucuna puriens* var. *utilis*, *Coix lacrymo-jobi*, *Lagerstrpomia speciosa*, Californian poppy, *Sparassis crispa*, *Cassia alata*, papaya, *Gnaphalium affine*, *Cassia occidentalis*, *Cnidium japonicum*, *Rosa rugosa*, glehnia root, rose, jackfruit, *Aspidistra elatior*, *Curcuma aromatica*, potato, palo azul, *Scutellaria barbata*, handaikai, Oregon grape, English holly, *Parietaria micrantha*, *Torreya nucifera*, hishinomi, *Verbena xhybrida*, hyssop, daisy, *Papaver rhoeas*, *Chamaecyparis obtusa*, *Fucus evanescens*, Himalayan ginseng, sunflower, caraway, *Erigeron annuus*, *Vinca minor*, *Amomum kravanh*, *Lagenaria leucantha* var. *gourda*, *Solanum lyratum*, *Calystegia japonica*, Bilberry, *Verbascum thapsus*, Japanese loquat, areca, *Piper kadzura*, pueraria mirifica, bukatou, *Tussilago farfara*, *Lagenaria leucantha* var. *depressa*, *Wistaria brachybotrys*, *Citrus medica*, hutabamukusa, *Beta vulgaris* var. *vulgaris*, buchu, bush tea, *Hibiscus rosa-sinensis*, grape, black cumin, black cohosh, blackberry, black root, *Pinus cembroides*, *Plantago ovata*, bryonia, blueberry, *Citrus hystrix*, *Citrus maxima*, dish wash gourd, monascus, safflower, *Crassocephalum crepidioides*, *Plantago lanceolata*, heruniariasou, *Aegle marmelos*, hyacinth-bean, rue, *Lippia citridora*, *Impatiens balsamina*, hawkweed, *Choenomeles speciosa*, dandelion, *Psoralea corylifolia*, *Tilia migueliana*, peony, hop, jojoba, bold, boroho, white sage, *Cirsium sieboldii*, marsh, *Grifora frondosa*, maiten, maka, *Clerodendron cyrtophyllum*, *Zizania latifolia*, machiko, pine, *Tricholoma matsutake*, *Ilex Paraguaynensis*, sweet marjorum, milk thistle, *Mentha rotundifolia*, mulberry, mandarin, purple loosestrife, *Polygonum aviculare*, *Acacia baileyana*, *Lotus corniculatus* var. *japonicus*, mint, muirapuama, *Sapindus mukurossi*, *Ophelia pseudo-chinensis*, pennyroyal, *Acer nikoense*, *Phellinus linteus*, *Ocimum basilicum*, evening primrose, lemon balm, melon, *Actinidia polygama*, *Pseudocydonia sinensis*, mosshokushi, peach, *Terminalia catappa*, *Cirsium dipsacolepis*, Jew's mallow, yacon, Indian mulberry, *Hydrangea grosseserrata*, cornflower, palm, *Ribes ambiguum*, *Fraxinus mandshurica*, willow, *Epilobium angustifolium*, Irish moss, *Carpesium abrotanoides*, *Rhus trichocarpa*, yam, *Anaphalis margaritacea*, *Rosa davurica*, *Kerria japonica*, *Hericium erinaceus*, *Vitis coignetiae*, *Lagenaria leucantha* var. *clavata*, eucalyptus, *Thamnolia vermicularis*, citron, *Daphniphyllum macropodum*, yucca, lily, *Plantago major*, *Viburnum prunifolium*, *Rumex japonicus*, European sokuzu, indiangooseberry, mugwort, *Chrysanthemum vulgare*, *Omphalia lapidescens*, *Rophanus sativus*, rye, lo han kuo, rasugurabura, raspberry, peanut, jute, ravensara, lavender, rambutan, *Dimocarpus longan*, *Artcmisia anomala*, *Strobilanthes cusia*, *Campsis grandiflora*, green gram, rooibos, borage, *Anagallis arvensis*, larkspur, *Ganoderma lucidum*, reonurususou, lemongrass, lemon thyme, astragal, *Desmodium styracifolium*, *Lathyrus quinguenervius*, rosehip, rosemary, roman chamomile, lovage, wild cherry, wild lettuce, horseradish.

The plants described in Notification No. 243 issued by Director General of Pharmaceutical Bureau, the Ministry of Health, Labor and Welfare, "On Revision of the Criterion for the Scope of Pharmaceuticals", Attachment 2, "List of Component Essence (Raw Materials) Used Exclusively as Pharmaceuticals" include *Fraxinus lanuginosa*, Arabian chanoki, Arabian motsuyaku, arnica, *Taxus cuspidate*, *Colchicum autumnale*, irisu, *Clematis chinensis*, *Artemisia capillaries*, Indian gerbera, snake wood, *Ficus religiosa*, *Epimedium grandiflorum* var. *thunbergianum*, *Aristolochia debilis*, *Lindera strychnifolia*, bearberry, *Rosa multiflora*, *Cytisus scoprius*, *Corydalis turtschaninovii*, *Sophora japonica*, oukashi, *Plantago asiatica*, *Astragalus membranaceus*, *Scutellaria baicalensis*, *Phello-dendron amurense*, *Prunus jamasakura*, *Coptis japonica*, *Dryopteris crassirhizoma*, oninosu, *Rohdea japonica*, *Polygala tenuifolia*, squill, *Erythrina variegata* var. *orientalis*, *Ampelopsis japonica*, *Prunella vulgaris* var. *lilacina*, *Terminalia chebula*, *Polygonum multiflorum*, *Rhamnus purshiana*, kakkou, *Pueraria lobata*, kabane, karabarumame, *Trichosanthes kirilowii* var. *japonica*, Carolina jasmine, *Coriolus versicolor*, *Nardostachys chinensis*, coltsfoot, kanboui, kanran, *Catalpa ovata*, *Citrus leiocarpa*, *Cinchona succirubra*, *Notopterygium incisum*, *Prunus armeniaca* var. *ansu*, *Strophantus dichotomus*, *Sophora flavescens*, *Mallotus philippinensis*, gurifonia sinpurisifoira, *Schizonepeta tenuifolia*, *Papaver somniferum*, *Pharbitis nil*, *Scrophularia buergeriana*, yellow gentian, *Geranium thunbergii*, *Cyperus rotundus*, *Gelsemium elegans*, *Magnolia officinalis*, *Ligusticum sinense*, *Picrorhiza kurrooa*, goldenseal, *Vaccinium vitis-idaea*, *Achyranthes japonica*, *Evodia rutaecarpa*, *Polygonum cuspidatum*, *Rhus java*, great burdock, *Schisandra chinensis*, *Citrullus colocynthis*, columba, konzurango, *Bupleurum chinense*, *Asarum sieboldii*, Sabina, *Cynomorium songaricum*, *Toddalia asiatica*, gerbera, *Lobelia sessilifolia*, *Smilax grabra*, *Physalis alkekengi* var. *francheti*, *Euchresta japonica*, *Rehmannia glutinosa*, *Aster tataricus*, digitalis, *Illicium religiosum*, *Lycium chinense*, *Arnebia euchroma*, *Tribulus terrestris*, *Diospyros kaki*, *Paeonia lactiflora*, *Cnidium monnieri*, *Amomum xanthioides*, *Acorus calamus* var. *asiaticus*, *Quescus acutissima*, *Cimicifuga foetida*, Indian poke, *Magnolia kobus*, *Aquilaria agallocha*, *Menyanthes trifoliate*, skullcap, *Convallaria majalis* var. *keiskei*, *Artemisia apiacea*, English hawthorn, *Aesculus turbinate*, *Viscum album* var. *coloratum*, *Pyrrosia lingua*, *Lycoris radiata*, *Acorus gramineus*, *Rhododendron degronianun*, *Dendrobium moniliforme*, snake root, *Cnidium officinale*, *Angelica decursiva*, *Nuphar japonicum*, *Rubia argyi*, common centaury, *Melia azedarach*, *Alexandria senna*, *Inula japonica*, *Swertia japonica*, *Amomum tsao-ko*, jequirity, *Xanthium strumarium*, *Atractylodes lancea*, *Orobanche coerulescens*, white mulberry, *Aralia alata*, *Dipsacus asper*, *Cycas revoluta*, sappan wood, *Rhamnus japonica* var. *decipiens*, *Rheum officinale*, *Cirsium japonicum*, betel, *Alisma plantago-aquatica* var. *orientale*, *Turnera diffusa*, tayuya, *Aralia elata*, *Salvia miltiorrhiza*, *Phyllostachys nigra*var. *henonis*, *Panax japonicus*, *Anemarrhena asphodeloides*, *Sanguisorba officinalis*, *Datura metel*, *Uncaria hirsuta*, *Polyporus umbellatus*, *Arisaema consanguineum*, *Gastrodia elata*, *Asparagus cochinchinensis*, wax gourd, *Angelica sinensis*, *Codonopsis pilosula*, *Juncus effuses* var. *decipiens*, toutsurukinbai, *Prunus persica* var. *davidiana*, touryousou, *Aralia cordata*, ipecac root, *Cuscuta australis*, gutta-perca tree, elecamane, *Aconitum japonicum*, nandia, corn, *Picrasma quassioides*, *Cistanche salsa*, Madagascar periwinkle, *Boswellia carterii*, *Ligustrum lucidum*, *Veratrum grandiflorum*, *Patrinia scabiosaefolia*, *Fritillaria verticillata* var. *thunbergii*, hakushijin, *Dictamnus dasycarpus*, *Pulsatilla cernua*, hakutousugi, *Ophiopogon japonicus*, *Morinda officinalis*, *Scopolia japonica*, croton oil plant, Virginian witch hazel, bariera, harumara, *Pinellia ternata*, castor bean, *Angelica anomala*, *Atractylodes chinensis*, *Santalum album*, *Stemona japonica*, *Hyoscyamus niger*, *Adonis amurensis*, bukushinboku, *Rubus chingii*, *Poria cocos*, hujikobu, hutabaaoi, *Rhamnus frangula*, belladonna, *Sinomenium acutum*, *Imperata cylindrica* var. *koenigii*, *Impatiens balsamina*, *Pteris multifida*, *Saposhnikovia divaricata*, *Typha angustata*, *Paeonia suffruticosa*, podofirumu, *Ephedra sinica*, *Digenea simplex*, *Cannabis sativa*, strychine, aztec tobacco, *Vitex rotundifolia*, mandrake, *Lobelia chinensis*, *Buddleja officinalis*, mimisenna, muira puama, *Siegesbeckia pubescens*, mouooren, *Equisetum hyemale*, *Akebia quinata*, *Momordica cochinchinensis*, *Saussurea lappa*, *Commiphora abyssinica*, *Amomum villosum*, *Leonurus sibiricus*, *Carpesium abrotanoides*, *Jaborandi Folium*, yarappa, yukinohana, yu-kiwarisou, *Myrica rubra*, yohinbe, rhatania, *Eupatorium fortunei*, *Gentiana scabra* var. *buegeri*, ryuunou, *Prunus mandshurica, Forsythia suspense*, rouhakuka, *Pyrola rotundifolia* subsp. *chinensis, Phragmites communis*, Indian tobacco.

Examples of the plants belonging to the genus *Hydrangea* are *Hydrangea macrophylla* Seringe, *Hydrangea mavrophylla* Seringe var. *otaksa Makino, Hydrangea macrophylla* Seringe subsp. *serrata Makino* var. *japonica Makino, Hydrangea macrophylla* Seringe subsp. *serrata Makino* var. *acuminata Makino, Hydrangea scandens* Seringe, *Hydrangea hirata* Sieb. et Zucc, *Hydrangea involucrata* Sieb., *Hydrangea sikokiana* Maxim., *Hydrangea paniculata* Sieb., *Hydrangea petiolaris* Sieb. et Zucc., *Hydrangea macrophylla* Seringe subsp. *serrata Makino* var. *amoena Makino, Hydrangea macrophylla* Seringe subsp. *serrata Makino* var. *angustata Makino*, and *Hydrangea macrophylla* Seringe var. *Thunbergii Makino*. Among them, *Hydrangea macrophylla* Seringe var. *Thunbergii Makino* is preferably employed.

As the plant containing an active ingredient, those as described, for example, in Pharmacopoeia Japan can be employed.

Examples of the plant as described in Pharmacopoeia Japan are gambir, powdered gambir, opium, powdered opium, Hydrangeae Dulcis Folium, powdered Hydrangeae Dulcis Folium, aloe, powdered aloe, fennel, bearberry leaf, powdered rose fruit, corydalis tuber, astragalus root, scutellaria root, powdered scutellaria root, phellodendron bark, powdered phellodendron bark, coptis rhizome, powdered coptis rhizome, polygala root, powdered polygala root, kaolin, prunella spike, zedoary, pueraria root, Japanese valerian, powdered Japanese valerian, trichosanthes root, glycyrrhiza, powdered glycyrrhiza, platycodon root, powdered platycodon root, catalpa fruit, immature orange, apricot kernel, sophora root, powdered sophora root, schizonepeta spike, cinnamonbark, powdered cinnamonbark, cassia seed, pharbitis seed, gentian, powdered gentian, geranium herb, powdered geranium herb, red ginseng, cyperus rhizome, powdered cyperus rhizome, magnolia bark, powdered magnolia bark, oriental bezoar, achyranthes root, evodia fruit, condurango, calumba, powdered calumba, bupleurum root, asiasarum root, smilax rhizome, powdered smilax rhizome, gardenia fruit, powdered gardenia fruit, cornus fruit, zanthoxylum fruit, powdered zanthoxylum fruit, dioscorea rhizome, rehmannia root, digitalis, powdered digitalis, lithospermum root, peony root, powdered peony root, plantago seed, plantago herb, houttuynia herb, ammomum seed, powdered ammomum seed, powdered ginger, cardamon, cimicifuga rhizome, senega, powdered senega, cnidium rhizome, powdered cnidium rhizome, nuphar zhizome, toad venom, senna leaf, powdered senna leaf, swertia herb, powdered sertia herb, atractylodes lancea rhizome, powdered atractylodes lancea rhizome, mulberry bark, perilla herb, powdered rhubarb, jujube, alisma rhizome, powdered alisma rhizome, panax rhizome, powdered panax rhizome, anemarrhena rhizome, clove, powdered clove, chuling, citrus unshiu peel, capsicum, powdered capsicum, Japanese angelica root, powdered Japanese angelica root, peach kernel, bitter orange peel, ipecac, powdered ipecac, tragacanth, powder tragacanth, picrasma wood, powdered picrasma wood, ginseng, ophiopogon tuber, mentha herb, glehnia root, angelica dahurica root, atractylodes rhizome, powdered atractylodes rhizome, sinomenium stem, imperata rhizome, saposhnikovia root, moutan bark, powdered moutan bark, mux vomica, ephedra herb, akebia stem, saussurea root, bitter cardamon, coix seed, powdered coix seed, Japanese gentian, powdered Japanese gentian, forsythia fruit, and rosin.

There is no particular limitation as to the active ingredients as far as they are contained in the above-mentioned plant and can be extracted therefrom by an extraction method as mentioned below, and an ethanol-soluble component is preferred.

Examples of the active ingredient are hydrangenol extracted from a plant belonging to the genus *Hydrangea*, phyllodulcin extracted from *Hydrangea macrophylla* SERINGE var. *Thunbergii Makino*, e.g., Hydrangeae Dulcis Folium, curcumin extracted from turmeric, glabridine or glabrol extracted from licorice root, and apigenin extracted from parsley.

There is no particular limitation as to the method for extracting an active ingredient from the plant containing the active ingredient, and for example, extraction with various solvents or supercritical fluid extraction is applicable.

There is no particular limitation as to the solvents used for extraction of the plant as far as the active ingredient can be extracted therewith. Examples of the solvent includes aqueous media such as water, inorganic salt aqueous solution and buffer solutions, and organic solvents such as alcohol, hexane, toluene, petroleum ether, benzene, ethyl acetate, chloroform, dichloromethane, 1,1,2-trichloroethene, di-methylsulfoxide, and acetone, among which alcohol is preferred.

Water may be water, distilled water, deionized water, or pure water.

Examples the buffer solution are phosphate buffer and citrate buffer. The inorganic salt used in the aqueous solution of inorganic salt includes, for example, sodium chloride, potassium chloride, calcium chloride, and the like.

Examples of the alcohol are monohydric alcohols such as methanol, ethanol, propanol and butanol, and multi-hydric alcohols such as propylene glycol and glycerol, among which a monohydric alcohol is preferred, and particularly ethanol is preferred.

These solvents may be used alone or as a mixture. As the mixed solvent, water-containing alcohols are preferred. Water-containing monovalent alcohols are more preferred, and water-containing ethanol is particularly preferred.

In extracting an active ingredient from the plant containing the active ingredient, it is appropriate to use a solvent which is usable for foods and drinks or feeds, for example, water, water-containing ethanol, or anhydrous ethanol.

As the solvent, liquidized carbon dioxide or supercritical fluid carbon dioxide may also be used.

The liquid extract containing the active ingredient may be prepared by extraction with various solvents or by supercritical fluid extraction under a condition in which the active ingredient can be extracted from the plant containing the active ingredient. The obtained liquid extract may further be subjected to extraction with various solvents or to supercritical fluid extraction under a condition that the active ingredient can be extracted. When the active ingredient cannot be extracted or hardly extracted from the plant by extraction with various solvents or by supercritical fluid extraction, the resultant extraction residue may further be subjected to extraction with various solvents or to supercritical fluid extraction under a condition that the active ingredient can be extracted.

For example, when the plant containing an active ingredient is *Hydrangea macrophylla* Seringe var. *Thunbergii Makino*, e.g., Hydrangeae Dulcis Folium, in order to extract an ethanol-soluble component such as phyllodulcin, the plant is subjected to extraction with an aqueous medium, and the resulting extraction residue is further subjected to extraction with water-containing ethanol or anhydrous ethanol. As the plant, dried one is preferably used.

For extraction, the solvent may be used, for example, in an amount of 0.1 to 10,000 parts by weight preferably 1 to 100 parts by weight based on 1 part by weight of the plant. There is no particular limitation as to the extraction temperature, but the extraction is preferably carried out at 0 to 100° C., more preferably 20 to 90° C. There is no particular limitation as to the time for extraction, but it may preferably be conducted, for example, for a period of 1 minute to 1 week, more preferably 30 minutes to 1 day.

There is no particular limitation as to the apparatus used for extraction, and a vessel designed for efficient extraction, a stirrer, a reflux condenser, a Soxhlet extractor, a homogenizer, a shaker, a supersonic generator, etc., may be used.

The liquid extract may be treated by means of various solid-liquid separation such as sedimentation, cake filtration, clear filtration, centrifugal filtration, centrifugal sedimentation, compression separation or filter press.

The plant powder may be the same one as that used for extraction of an active ingredient or powder of a different species of plant. For example, when the extract containing an active ingredient is of Hydrangeae Dulcis Folium, the plant powder of Hydrangeae Dulcis Folium, green tea, turmeric, and so on may be preferably used.

Examples of the plant used for preparing the plant powder are those as described in Notification No. 243 issued by Director General of Pharmaceutical Bureau, the Ministry of Health, Labor and Welfare, "On Revision of the Criterion for the Scope of Pharmaceuticals", Attachment 3, "List of Component Essence (Raw Materials) Recognized as Foods as far as their indication as pharmaceuticals is not advocated"; those as described in Notification No. 243 issued by Director General of Pharmaceutical Bureau, the Ministry of Health, Labor and Welfare, "On Revision of the Criterion for the Scope of Pharmaceuticals", Attachment 2, "List of Component Essence (Raw Materials) Used Exclusively as Pharmaceuticals"; and those belonging to the genus *Hydrangea*.

The plant used for preparing the plant powder includes, for example, those described in Pharmacopoeia Japan.

For preparing the plant powder, all of the parts of plant may be used, for example, leaves, flowers, branches, stems, fruits, roots, seeds, cultured cells or organs, or callus. Particularly, the parts in which the plant tissue such as vessel can be observed with a microscope, for example, leaves, branches, stems and roots, are preferred. These parts may be used as such or after being treated physically or chemically or biologically.

Examples of the method of physical or chemical treatment are drying, freeze-drying, disruption, and extraction. The physically or chemically treated matters include dried matters, freeze-dried matters, disrupted matters and extracted matters. The extracted matters include the residue of the plant obtained after the extraction.

An example of the method of the biological treatment is fermentation, and biologically treated matters include fermented matters.

For preparing the plant powder, the plant, preferably dried plant, is crushed with a compression crusher such as jaw crusher, gyratory crusher or cone crusher; shearing machine such as cutter mill or shredder; impact crusher such as hammer crusher; roll mill such as roll crusher; rotary mill such as disintegrator or cage mill; screw mill such as coffee mill; rolling mill such as edge runner; hammering mill such as stamp mill; roller mill such as centrifugal roller mill, ball bearing mill, bowl mill, zego mill, or ong mill; high speed rotary mill such as swing hammer mill, pin mill, cage mill, turbo-type mill, or centrifugal mill; vessel vibrating mill such as rolling ball mill, vibrating ball mill, planetary ball mill, or CF mill; jet mill such as flow-pipe type mill, stirring tank mill, annular-type mill, air suction type mill, impact plate impact miller, or fluidized bed mill; crusher such as ultrasonic shredder; stone mortar or mortar.

The product obtained by the above method may further be processed physically or chemically to give plant powder.

The average particle size of the plant powder is preferably 0.1 µm to 1 mm, more preferably 1 to 100 µm, and particularly 2 to 50 µm in a dry state, though there is no particular limitation as far as they are fine particle.

The average particle size of the plant powder in a dry state can be determined, for example by a laser diffraction particle distribution analyzer.

Alternatively, when the plant powder is swelled with a 1:1 mixture of glycerol and water, the average particle size of the powder is preferably 1 µm to 10 mm, more preferably 10 µm to 1 mm, and particularly 20 to 500 µm.

The average particle size of the plant powder in a swelling state can be determined, for example by observation with a microscope.

In the present invention, the liquid extract containing an active ingredient is concentrated in the presence of the plant powder.

The plant powder may be added during the step of extraction of the active ingredient from the plant or before the step of concentration of the liquid extract, so long as the plant powder exists in the liquid extract during the course of concentration before adhesion of the precipitated extract on the wall of a concentration vessel or before deposition of the precipitate of the extract. Preferably, the plant powder is added to the liquid extract before concentration.

In concentrating the liquid extract containing an active ingredient, the amount of the plant powder to be added is not particularly limited, however, the amount is preferably 19 to 1/19 parts by dry weight, more preferably 9 to 1/9 parts by dry weight, particularly 3 to 1/3 parts by dry weight for 1 part by dry weight of the active ingredient contained in the liquid extract.

Methods of concentrating the liquid extract containing an active ingredient include concentration under heating and reduced pressure, concentration under heating and atmospheric pressure, concentration with a spray drier or with drum drier and concentration by freeze-drying, among which concentration under heating and reduced pressure is preferred.

According to the present invention, even if a liquid extract containing an active ingredient is concentrated to such an extent that precipitate is yielded in the liquid extract by the concentration without adding the plant powder, precipitates are not yielded and a plant powder-containing liquid plant extract with excellent fluidity can be obtained.

The obtained plant powder-containing liquid plant extract is dried, without any treatment or after being allowed to stand and removing the upper layer, to thereby obtain a plant powder-containing plant extracted.

The method of drying includes drying under heating and reduced pressure, drying under heating and atmospheric pressure, or drying with a spray drier or with drum drier, or freeze-drying, among which drying under heating and reduced pressure or freeze-drying is preferred.

The dry product obtained by the present invention can easily be pulverized by a convenient method for pulverizing a plant, for example, compression or rolling with hands.

In the present invention, the content (% by weight) of the active ingredient in the dry product from the liquid plant extract contained in the plant powder-containing liquid plant extract or that in the dry product from the plant extract contained in the plant powder-containing plant extract may be at least the content (% by weight) of the active ingredient contained in the dry plant used for extraction, and preferably 2 times or more, more preferably 5 times or more, and particularly 10 times or more.

The dry products of the liquid plant extract, the plant extract, and the plant used for extraction may be prepared respectively from the liquid plant extract contained in a plant powder-containing liquid plant extract, the plant extract contained in a plant powder-containing plant extract, and the plant used for extraction, by drying, for example, drying under heating and reduced pressure, drying under heating and atmospheric pressure, freeze-drying, and the like, up to 10% by weight or lower of moisture content.

When Hydrangeae Dulcis Folium are used as a plant containing active ingredients, phyllodulcin, one of the active ingredients, is usually contained in the amount of 1 to 1.5% by weight in the dry product of Hydrangeae Dulcis Folium. Therefore, the content of phyllodulcin in the dry product produced from the liquid extract or extract of Hydrangeae Dulcis Folium containing plant powder or the plant extract containing plant powder of the present invention may be higher than 1 to 1.5% by weight, preferably 2% by weight or higher, more preferably 5% by weight or higher.

The contents of the plant powder of the present invention in the liquid plant extract or plant extract containing plant powder may be 19 to 1/19 parts by dry weight, more preferably 9 to 1/9 parts by dry weight, particularly 3 to 1/3 parts by dry weight to 1 part by dry weight of the active ingredient in the liquid extract or plant extract.

The liquid plant extract or plant extract containing plant powder of the present invention contains plant powder, in which the content of the active ingredient therein is higher than that in the plant containing the active ingredient, which can easily be pulverized.

Although there is no limitation as to the components of the liquid plant extract or plant extract containing plant powder of the present invention, it is preferred that an ethanol-soluble component is contained therein, and its amount is preferably 20% by weight or more, more preferably 30% by weight or more.

The content (% by weight) of the ethanol-soluble component in the liquid plant extract and plant extract containing plant powder of the present invention can be determined according to the following method.

The liquid plant extract or plant extract containing plant powder as a sample for analysis (70 mg) is precisely weighed in a 2 ml polypropylene tube, and 1.4 ml of guaranteed grade ethanol is added thereto to give a 50 mg/ml solution. When the analyte is a liquid extract, it is dried under reduced pressure, and the resulting solid powder is used as a sample for analysis. The tube is capped, then occasionally shaken at 40°C. for 1 hour to percolate, and centrifuged at 12,000 rpm for 5 minutes to separate a supernatant from precipitate. The supernatant (1 ml) is evaporated to dryness, and the weight of the ethanol-soluble component is measured. The dry weight of the sample is obtained by subtracting the dry weight loss from the sample weight to calculate the content of the ethanol-soluble component. The dry weight loss may be determined as follows. An analytical sample (2 to 6 g) is placed in a weighing bottle of which the weight has been determined in advance, and the weight is precisely determined. After drying at 105° C. for 6 hours, this is precisely weighed to obtain the weight loss by drying.

The presence of the plant powder in the plant extract containing plant powder of the present invention can be confirmed by observation with a microscope equipped with an eye lens of 10 magnifications and with an object lens of 40 magnifications, for example according to the following procedure.

To 0.1 g of the powdered analytical sample was dropwise added a few drops of a 1:1 mixture of glycerol and water; the mixture is stirred well with a small glass stick without generating no foam and allowed to stand for 10 minutes or longer to make the sample swell. A small quantity of the swelled sample is smeared on a slide glass with a tip of a glass stick, on which is then dropped one drop of the 1:1 mixture of glycerol and water. The smear is spread nearly evenly so that tissue pieces are not overlapped, and carefully covered with a cover glass so that no foam is taken therein.

In observation of the slide glass with a microscope, when a parenchyma comprised of orbicular or polygonal cells, upper and under epidermis, and vessels are observed, particularly when vessels are observed, it can be confirmed that there is contained plant powder. The vessels may have a pattern such as annellation, spiral, reticulate, pitted or scalariform.

There is no particular limitation as to foods and drinks or feeds to which the liquid plant extract or plant extract containing plant powder of the present invention is added.

Examples of the foods and drinks to which the liquid plant extract or plant extract containing plant powder of the present invention is added are juice, soft drinks, soup, tea, dairy products such as lactic acid bacteria beverages, fermented milk, ice cream, butter, cheese, yogurt, processed milk and skim milk, meat products such as ham, sausage and hamburger, fish products, egg products such as Dashimaki (omelet with stock) and Tamago-dofu (steamed beaten egg with soup stock), confectionary such as cookies, jelly, snacks and chewing gum, bread, noodles, pickles, smoked fish and meat, dry fish, Tsukudani (simmered meat in soy sauce and sugar), and seasonings.

The form of the foods and drinks includes, for example, powdered foods, sheet-shaped foods, bottled foods, canned foods, retort foods, capsule foods, tablet foods, liquid foods, drinkable preparations, and the like.

The feeds to which the liquid plant extract or plant extract containing plant powder of the present invention may be added are exemplified by those which can be fed to animals including mammals, birds, reptiles, amphibians and fishes, for example, those which can be used for pets such as dog, cat or mouse, domestic animals such as cattle or pig, poultry such as chicken or turkey, or hatchery fishes such as sea bream or young yellowtail. Also included are feeds comprising raw materials for feeds, for example, grains, bran, vegetable oil cakes, animal feed materials, and other feed materials and purified products.

Examples of the grains are milo, wheat, barley, oats, rye, brown rice, buckwheat, foxtail millet, broomcorn millet, Japanese millet, corn and soybean.

Example of the bran are rice bran, defatted rice bran, wheat bran, wheat middlings, wheat germ, barely bran, screening, pellets, corn bran and corn germ.

Examples of the vegetable oil cakes are soybean oil cake, soybean flour, linseed oil cake, cotton seed oil cake, peanut oil cake, safflower oil cake, coconut oil cake, palm oil cake, sesame oil cake, sunflower oil cake, rapeseed oil cake, kapok oil cake and mustard oil cake.

Examples of the animal feed materials are fish meal (northern ocean meal, imported meal, whole meal and coast meal), fish soluble, meat meal, meat and bone meal, blood powder, degenerated hair, bone meal, treated by-product for livestock, feather meal, silk-worm pupa, skim milk, casein and dry whey.

Example of the other feed materials are stems and leaves of the plant(e.g., alfalfa, hay cube, alfalfa leaf meal, and powder of false acacia), processed industrial by-products of corn (e.g., corn gluten, meal, corn gluten feed and corn steep liquor), processed starch product (e.g., starch), sugar, fermentation industrial products (e.g., yeast, beercake, malt root, alcohol cake and soy source cake), agricultural by-products (e.g., processed citrus fruit cake, tofu cake, coffee cake and cocoa cake) and others (e.g. cassava, broad bean, guar meal, sea weed, krill, spirulina, chlorella and minerals).

Examples of the purified products are proteins (e.g., casein and albumin), amino acids, sugars (e.g., starch, cellulose, sucrose and glucose), minerals and vitamins.

The following examples and comparative examples will explain the present invention in more detail, but they are not intended to limit the scope of the present invention.

EXAMPLE 1

Hydrangeae Dulcis Folium (10 g) (Shihira Shoten) was extracted with 200 ml of 30% ethanol [ethanol of guaranteed grade (Kishida Chemical Co., Ltd.) diluted with pure water] under occasional stirring at 40° C. for 2 hours and then filtered through a MIRACLOTH (CALBIOCHEM) to give 180 ml of 30% ethanol extract of Hydrangeae Dulcis Folium. The liquid extract (1 ml) was freeze-dried to give 17.1 mg of dry product of which the moisture content was 10% or lower and the phyllodulcin content was 0.537 mg/ml.

To the liquid extract (180 ml) was added 0.4 g of powder of Hydrangeae Dulcis Folium (Yasuma Co.), and concentrated in a rotary evaporator under heating in vacuo to give 20 ml of concentrate. This concentrate put into a 50 ml-beaker and allowed to stand to yield a homogeneous fluid suspension at the bottom of the beaker. There was recognized no generation of taffy-like precipitate. The suspension could easily be put to a lyophilizer and freeze-dried to give a highly disintegrable solid dry product. The obtained dry product was pulverized by kneading with hands to give powder of Hydrangeae Dulcis Folium extract containing Hydrangeae Dulcis Folium powder.

The obtained powder contained about 89% Hydrangeae Dulcis Folium extract by weight and 3.0% phyllodulcin by weight.

In this connection, the *Hydrangeae* Dulcis Folium (Shihira Shoten) used for extraction contained 1.55% phyllodulcin by weight, and the Hydrangeae Dulcis Folium powder (Yasuma Co.) contained 1.0% phyllodulcin by weight.

The Hydrangeae Dulcis Folium powder was found to contain 10% by weight of ethanol-soluble component with measurement in the following method.

The sample (about 70 mg, dryweight) was precisely weighed in a 2 ml polypropylene tube, to which was then added about 1.4 ml of guaranteed grade ethanol to give a 50 mg/ml solution. The tube was capped, then occasionally shaken at 40° C. for 1 hour to percolate, and centrifuged at 12,000 rpm for 5 minutes to separate a supernatant from precipitate. The supernatant (1 ml) was evaporated to dryness, and measured the weight of the ethanol-soluble component. Thus, the rate (% by weight) of the ethanol-soluble component to the weight of the sample was calculated.

In addition, the Hydrangeae Dulcis Folium powder was confirmed to have vessels by observation with a microscope as follows.

To 0.1 g of the powdered sample was dropwise added 3 drops of a 1:1 mixture of glycerol and water, which was stirred well with a small glass stick without generating foam, and allowed to stand for 10 minutes or longer to make the sample swell. A small quantity of the swelled sample was smeared on a slide glass with a tip of a glass stick, on which was then dropped one drop of a 1:1 mixture of glycerol and water. The smear was spread nearly evenly so that tissue pieces were not overlapped and carefully covered with a cover glass so that no foam was taken therein. The slide glass was observed with a microscope equipped with an eye lens of 10 magnifications and an object lens of 40 magnifications.

Additionally, as for the Hydrangeae Dulcis Folium powder, the particle size in a dry state was determined with a laser diffraction particle distribution analyzer (Particle Size Analyzer; JEOL HELOS & LODOS), which indicated the average particle size was 5.5 μm.

EXAMPLE 2

Hydrangeae Dulcis Folium (10 g) (Shihira Shoten) was extracted with 200 ml of 40% ethanol [ethanol of guaranteed grade (Kishida Chemical Co., Ltd.) diluted with pure water] under occasional stirring at 40° C. for 2 hours and then filtered through a MIRACLOTH (CALBIOCHEM) to give 180 ml of 40% ethanol extract of *Hydrangea*e Dulcis Folium. The liquid extract (1 ml) was freeze-dried to give 17.5 mg of dry product of which the moisture content was 10% or lower and the phyllodulcin content was 0.763 mg/ml.

To the liquid extract (180 ml) was added 0.4 g of powder of Hydrangeae Dulcis Folium (Yasuma Co.), and concentrated in a rotary evaporator under heating in vacuo to give 30 ml of concentrate. This concentrate was put into a 50 ml-beaker and allowed to stand to yield a homogeneous fluid suspension at the bottom of the beaker. There was recognized no generation of taffy-like precipitate. The suspension could easily be put to a lyophilizer, and freeze-dried to give a highly disintegrable solid dry product. This was pulverized by kneading with hands to give powder of Hydrangeae Dulcis Folium extract containing Hydrangeae Dulcis Folium powder.

This powder contained about 89% Hydrangeae Dulcis Folium extract by weight and 4.0% phyllodulcin by weight.

EXAMPLE 3

Hydrangeae Dulcis Folium (10 g) (Shihira Shoten) was extracted with 200 ml of 50% ethanol [ethanol of guaranteed grade (Kishida Chemical Co., Ltd.) diluted with pure water] under occasional stirring at 40° C. for 2 hours and then filtered through a MIRACLOTH (CALBIOCHEM) to give 180 ml of 50% ethanol extract of Hydrangeae Dulcis Folium. The liquid extract (1 ml) was freeze-dried to give 16.5 mg of dry product of which the moisture content was 10% or lower and the phyllodulcin content was 0.853 mg/ml.

To the liquid extract (180 ml) was added 0.4 g of powder of Hydrangeae Dulcis Folium (Yasuma Co.), and concentrated in a rotary evaporator under heating in vacuo to give 30 ml of concentrate. This concentrate was put into a 50-ml beaker and allowed to stand to yield a homogeneous fluid suspension at the bottom of the beaker. There was recognized no generation of taffy-like precipitate. The suspension could easily be put to a lyophilizer and freeze-dried to give a highly disintegrable solid dry product. This was pulverized by kneading with hands to give powder of Hydrangeae Dulcis Folium extract containing Hydrangeae Dulcis Folium powder.

This powder contained about 89% Hydrangeae Dulcis Folium extract by weight and 4.7% phyllodulcin by weight.

EXAMPLE 4

Hydrangeae Dulcis Folium (10 g) (Shihira Shoten) was extracted with 200 ml of 60% ethanol [ethanol of guaranteed grade (Kishida Chemical Co., Ltd.) diluted with pure water] under occasional stirring at 40° C. for 2 hours and then filtered through a MIRACLOTH (CALBIOCHEM) to give 180 ml of 60% ethanol extract of Hydrangeae Dulcis Folium. The liquid extract (1 ml) was freeze-dried to give 14.9 mg of dry product of which the moisture content was 10% or lower and the phyllodulcin content was 0.861 mg/ml.

To the liquid extract (180 ml) was added 0.4 g of powder of Hydrangeae Dulcis Folium (Yasuma Co.), and concentrated in a rotary evaporator under heating in vacuo to give 30 ml of concentrate. This concentrate was put into a 50 ml-beaker and allowed to stand to yield a homogeneous fluid suspension at the bottom of the beaker. There was recognized no generation of taffy-like precipitate. The suspension could easily be put to a lyophilizer and freeze-dried to give a highly disintegrable solid dry product. This was pulverized by kneading with hands to give powder of Hydrangeae Dulcis Folium extract containing Hydrangeae Dulcis Folium powder.

This powder contained about 89% Hydrangeae Dulcis Folium extract by weight and 5.2% phyllodulcin by weight.

COMPARATIVE EXAMPLE 1

Hydrangeae Dulcis Folium (10 g) (Shihira Shoten) was extracted with 200 ml of 30% ethanol [ethanol of guaranteed grade (Kishida Chemical Co., Ltd.) diluted with pure water] under occasional stirring at 40° C. for 2 hours and then filtered through a MIRACLOTH (CALBIOCHEM) to give 180 ml of 30% ethanol extract of Hydrangeae Dulcis Folium. The liquid extract to which was added nothing was concentrated in a rotary evaporator under heating in vacuo to give 20 ml of concentrate. This concentrate was put into a 50 ml-beaker and allowed to stand for 30 minutes to yield a taffy-like precipitate at the bottom of the beaker. This precipitate had no fluidity and homogeneity. This precipitate was stuck on the bottom of the beaker and could not be dispersed by shaking. Therefore, it was not easy to put the precipitate into a lyophilizer. Lyophilization of the precipitate gave hard tarry dry product, which was stuck inside a vessel of the lyophilizer and could not easily be recovered. The dried product could not be crushed by kneading with hands.

COMPARATIVE EXAMPLE 2

Hydrangeae Dulcis Folium (10 g) (Shihira Shoten) was extracted with 200 ml of 40% ethanol [ethanol of guaranteed grade (Kishida Chemical Co., Ltd.) diluted with pure water] under occasional stirring at 40° C. for 2 hours and then filtered through a MIRACLOTH (CALBIOCHEM) to give 180 ml of 40% ethanol extract of Hydrangeae Dulcis Folium. The liquid extract to which was added nothing was concentrated in a rotary evaporator under heating in vacuo to give 30 ml of concentrate. This concentrate was put into a 50 ml-beaker and allowed to stand for 30 minutes to yield a taffy-like precipitate at the bottom of the beaker. This precipitate had no fluidity and homogeneity. This precipitate was stuck on the bottom of the beaker and could not be dispersed by shaking. Therefore, it was not easy to put the precipitate into a lyophilizer. Lyophilization of the precipitate gave hard tarry dry product, which was stuck inside a vessel of the lyophilizer and could not easily be recovered. The dried product could not be crushed by kneading with hands.

COMPARATIVE EXAMPLE 3

Hydrangeae Dulcis Folium (10 g) (Shihira Shoten) was extracted with 200 ml of 50% ethanol [ethanol of guaranteed grade (Kishida Chemical Co., Ltd.) diluted with pure water] under occasional stirring at 40° C. for 2 hours and then filtered through a MIRACLOTH (CALBIOCHEM) to give 180 ml of 50% ethanol extract of Hydrangeae Dulcis Folium. The liquid extract to which was added nothing was concentrated in a rotary evaporator under heating in vacuo to give 30 ml of concentrate. This concentrate was put into a 50 ml-beaker and allowed to stand for 30 minutes to yield a taffy-like precipitate at the bottom of the beaker. This precipitate had no fluidity and homogeneity. This precipitate was stuck on the bottom of the beaker and could not be dispersed by shaking. Therefore, it was not easy to put the precipitate into a lyophilizer. Lyophilization of the precipitate gave hard tarry dry product, which was stuck inside a vessel of the lyophilizer and could not easily be recovered. The dried product could not be crushed by kneading with hands.

COMPARATIVE EXAMPLE 4

Hydrangeae Dulcis Folium (10 g) (Shihira Shoten) was extracted with 200 ml of 60% ethanol [ethanol of guaranteed grade (Kishida Chemical Co., Ltd.) diluted with pure water] under occasional stirring at 40° C. for 2 hours and then filtered through a MIRACLOTH (CALBIOCHEM) to give 180 ml of 60% ethanol extract of Hydrangeae Dulcis Folium. The liquid extract to which was added nothing was concentrated in a rotary evaporator under heating in vacuo to give 30 ml of concentrate. This concentrate was put into a 50-ml beaker and allowed to stand for 30 minutes to yield a taffy-like precipitate at the bottom of the beaker. This precipitate had no fluidity and homogeneity. This precipitate was stuck on the bottom of the beaker and could not be dispersed by shaking. Therefore, it was not easy to put the precipitate into a lyophilizer. Lyophilization of the precipitate gave hard tarry dry product, which was stuck inside a vessel of the lyophilizer and could not easily be recovered. The dried product could not be crushed by kneading with hands.

EXAMPLE 5

Hydrangeae Dulcis Folium (10 g) (Shihira Shoten) was extracted with 200 ml of 30% ethanol [ethanol of guaranteed grade (Kishida Chemical Co., Ltd.) diluted with pure water] under occasional stirring at 40° C. for 2 hours and then filtered through a MIRACLOTH (CALBIOCHEM) to give 180 ml of 30% ethanol extract of Hydrangeae Dulcis Folium. The liquid extract (1 ml) was freeze-dried to give 17.1 mg of dry product of which the moisture content was 10% or lower and the phyllodulcin content was 0.537 mg/ml.

To the liquid extract (180 ml) was added 0.4 g of powder of Hydrangeae Dulcis Folium (Yasuma Co.), and concentrated in a rotary evaporator under heating in vacuo to give 20 ml of concentrate. This concentrate was put into a 50 ml-beaker and allowed to stand to yield a homogeneous fluid suspension at the bottom of the beaker. There was recognized no generation of taffy-like precipitate. After standing, the upper layer (10 ml) of the concentrate was removed from the lower layer. The lower layer could easily be put to a lyophilizer and freeze-dried to give a highly disintegrable solid dry product. This was pulverized by kneading with hands to give 0.6 g of powder of Hydrangeae Dulcis Folium extract containing Hydrangeae Dulcis Folium powder.

This powder contained about 53% Hydrangeae Dulcis Folium extract by weight and 6.0% phyllodulcin by weight. As to this powder, the content of ethanol-soluble component was determined and the vessels were observed according to the method as described in Example 1. The content of the ethanol-soluble component was 25% by weight, and the vessels were observed.

EXAMPLE 6

Hydrangeae Dulcis Folium (10 g) (Shihira Shoten) was extracted with 200 ml of 40% ethanol [ethanol of guaranteed grade (Kishida Chemical Co., Ltd.) diluted with pure water] under occasional stirring at 40° C. for 2 hours and then filtered through a MIRACLOTH (CALBIOCHEM) to give 180 ml of 40% ethanol extract of Hydrangeae Dulcis Folium. The liquid extract (1 ml) was freeze-dried to give 17.5 mg of dry product of which the phyllodulcin content was 0.763 mg/ml.

To the liquid extract (180 ml) was added 0.4 g of powder of Hydrangeae Dulcis Folium (Yasuma Co.), and concentrated in a rotary evaporator under heating in vacuo to give 30 ml of concentrate. This concentrate was put into a 50 ml-beaker and allowed to stand to yield a homogeneous fluid suspension at the bottom of the beaker. There was recognized no generation of taffy-like precipitate. After standing, the upper layer (20 ml) of the concentrate was removed from the lower layer. The lower layer could easily be put to a lyophilizer and freeze-dried to give a highly disintegrable solid dry product. This was pulverized by kneading with hands to give 0.6 g of powder of Hydrangeae Dulcis Folium extract containing Hydrangeae Dulcis Folium powder.

This powder contained about 53% Hydrangeae Dulcis Folium extract by weight and 8.0% phyllodulcin by weight. As to this powder, the content of ethanol-soluble component was determined and the vessels were observed according to the method as described in Example 1. The content of the ethanol-soluble component was 34% by weight, and the vessels were observed.

EXAMPLE 7

Hydrangeae Dulcis Folium (10 g) (Shihira Shoten) was extracted with 200 ml of 50% ethanol [ethanol of guaranteed grade (Kishida Chemical Co., Ltd.) diluted with pure water] under occasional stirring at 40° C. for 2 hours and then filtered through a MIRACLOTH (CALBIOCHEM) to give 180 ml of 50% ethanol extract of Hydrangeae Dulcis Folium. The liquid extract (1 ml) was freeze-dried to give 16.5 mg of dry product of which the phyllodulcin content was 0.853 mg/ml.

To the liquid extract (180 ml) was added 0.4 g of powder of Hydrangeae Dulcis Folium (Yasuma Co.), and concentrated in a rotary evaporator under heating in vacuo to give 30 ml of concentrate. This concentrate was put into a 50 ml-beaker and allowed to stand to yield a homogeneous fluid suspension at the bottom of the beaker. There was recognized no generation of taffy-like precipitate. After standing, the upper layer (20 ml) of the concentrate was removed from the lower layer. The lower layer could easily be put to a lyophilizer and freeze-dried to give a highly disintegrable solid dry product. This was pulverized by kneading with hands to give 0.6 g of powder of Hydrangeae Dulcis Folium extract containing Hydrangeae Dulcis Folium powder.

This powder contained about 53% Hydrangeae Dulcis Folium extract by weight and 8.0% phyllodulcin by weight. As to this powder, the content of ethanol-soluble component was determined and the vessels were observed according to the method as described in Example 1. The content of the ethanol-soluble component was 34% by weight, and the vessels were observed.

EXAMPLE 8

Hydrangeae Dulcis Folium (10 g) (Shihira Shoten) was extracted with 200 ml of 60% ethanol [ethanol of guaranteed grade (Kishida Chemical Co., Ltd.) diluted with pure water] under occasional stirring at 40° C. for 2 hours and then filtered through a MIRACLOTH (CALBIOCHEM) to give 180 ml of 60% ethanol extract of Hydrangeae Dulcis Folium. The liquid extract (1 ml) was freeze-dried to give 14.9 mg of dry product of which the phyllodulcin content was 0.861 mg/ml.

To the liquid extract (180 ml) was added 0.4 g of powder of Hydrangeae Dulcis Folium (Yasuma Co.), and concentrated in a rotary evaporator under heating in vacuo to give 30 ml of concentrate. This concentrate was put into a 50 ml-beaker and allowed to stand to yield a homogeneous fluid suspension at the bottom of the beaker. There was recognized no generation of taffy-like precipitate. After standing, the upper layer (20 ml) of the concentrate was removed from the lower layer. The lower layer could easily be put to a lyophilizer and freeze-dried to give a highly disintegrable solid dry product. This was pulverized by kneading with hands to give 0.6 g of powder of Hydrangeae Dulcis Folium extract containing Hydrangeae Dulcis Folium powder.

This powder contained about 53% Hydrangeae Dulcis Folium extract by weight and 8.0% phyllodulcin by weight. As to this powder, the content of ethanol-soluble component was determined and the vessels were observed according to the method as described in Example 1. The content of the ethanol-soluble component was 38% by weight, and the vessels were observed.

EXAMPLE 9

Hydrangeae Dulcis Folium (20 g) (Shihira Shoten) was extracted with 400 ml of water with occasional stirring at 40° C. for 2 hours and then filtered through a MIRACLOTH (CALBIOCHEM) to give an extraction residue. This residue was extracted with 400 ml of 60% ethanol [ethanol of guaranteed grade (Kishida Chemical Co., Ltd.) diluted with water] under occasional stirring at 40° C. for 2 hours and then filtered through a MIRACLOTH to give an extract of Hydrangeae Dulcis Folium. The liquid extract (1 ml) was freeze-dried to give 4.5 mg of dry product of which the phyllodulcin content was 0.66 mg/ml. The phyllodulcin content in the Hydrangeae Dulcis Folium extract solution was 15% as a rate of the total solid portion.

To the liquid extract (about 400 ml) was added 1.6 g of powder of Hydrangeae Dulcis Folium (Yasuma Co.), and concentrated in a rotary evaporator under heating in vacuo to give 60 ml of concentrate. This concentrate was put into a 100 ml-beaker and allowed to stand for 30 minutes to yield a homogeneous fluid suspension at the bottom of the beaker. There was recognized no generation of taffy-like precipitate. After standing, the upper layer (40 ml) of the concentrate was removed from the lower layer (20 ml). The resulting lower layer could easily be put to a lyophilizer and freeze-dried to give a highly disintegrable solid dry product. This was pulverized by kneading with hands to give 2.5 g of powder of Hydrangeae Dulcis Folium extract containing Hydrangeae Dulcis Folium powder.

This powder contained about 55% Hydrangeae Dulcis Folium extract and 18.0% phyllodulcin by weight. As to this powder, the content of ethanol-soluble component was determined and the vessels were observed according to the method as described in Example 1. The content of the ethanol-soluble component was 50% by weight, and the vessels were observed.

EXAMPLE 10

The same procedure as in Example 9 was repeated except for adding 1.6 g of powder of green tea (Mino Shirakawa Ground Tea Co.) to about 400 ml of an extract of Hydrangeae Dulcis Folium, in stead of adding 1.6 g of Hydrangeae Dulcis Folium, and 60 ml of concentrate was obtained. The obtained concentrate was put into a 100 ml-beaker and allowed to stand for 30 minutes to yield a homogeneous fluid suspension at the bottom of the beaker. There was recognized no generation of taffy-like precipitate. After standing, the upper layer (40 ml) of the concentrate was removed from the lower layer (20 ml). The resulting lower layer could easily be put to a lyophilizer and freeze-dried to give a highly disintegrable solid dry product. This was pulverized by kneading with hands to give 2.5 g of powder of Hydrangeae Dulcis Folium extract containing green tea powder.

This powder contained 36% Hydrangeae Dulcis Folium extract by weight and 15.0% phyllodulcin by weight. As to this powder, the content of ethanol-soluble component was determined and the vessels were observed according to the method as described in Example 1. The content of the ethanol-soluble component was 53% by weight, and the vessels were observed.

Additionally, as for the green tea powder, the particle size in a dry state was determined by a laser diffraction particle distribution analyzer (Particle Size Analyzer; JEOL HELOS & LODOS), which indicated the average particle size was 4.4 µm.

EXAMPLE 11

The same procedure as in Example 9 was repeated except for adding 1.6 g of powder of powdered turmeric (Kaneka Sun Spice Co.) to about 400 ml of an extract of Hydrangeae Dulcis Folium, in stead of adding 1.6 g of Hydrangeae Dulcis Folium powder, and 60 ml of concentrate was obtained. The obtained concentrate was put into a 100 ml-beaker and allowed to stand for 30 minutes to yield a homogeneous fluid suspension at the bottom of the beaker. There was recognized no generation of taffy-like precipitate. After standing, the upper layer (40 ml) of the concentrate was removed from the lower layer (20 ml). The resulting lower layer could easily be put to a lyophilizer and freeze-dried to give a highly disintegrable solid dry product. This was pulverized by rolling with hands to give 2.5 g of powder of Hydrangeae Dulcis Folium extract containing powdered turmeric.

This powder contained 36% Hydrangeae Dulcis Folium by weight and 15.0% phyllodulcin by weight. As to this powder, the content of ethanol-soluble component was determined and the vessels were observed according to the method as described in Example 1. The content of the ethanol-soluble component was 53% by weight, and the vessels were observed.

Additionally, as for the powdered turmeric, the particle size in a dry state was determined by a laser diffraction particle distribution analyzer (Particle Size Analyzer; JEOL HELOS & LODOS), which indicated the average particle size was 31.7 µm.

COMPARATIVE EXAMPLE 5

The same procedure as in Example 9 was repeated except for adding 1.6 g of dry yeast (DIFCO) to about 400 ml of an extract of Hydrangeae Dulcis Folium, in stead of adding 1.6 g of Hydrangeae Dulcis Folium powder, and 60 ml of concentrate was obtained. The obtained concentrate was put into a 100-ml beaker and allowed to stand for 30 minutes to yield taffy-like precipitate at the bottom of beaker but not a highly fluid homogeneous suspension.

COMPARATIVE EXAMPLE 6

The same procedure as in Example 9 was repeated except for adding 1.6 g of cellulose (Oriental Yeast Co.) to about 400 ml of an extract of Hydrangeae Dulcis Folium, in stead of adding 1.6 g of Hydrangeae Dulcis Folium powder, and 60 ml of concentrate was obtained. The obtained concentrate was put into a 100-ml beaker and allowed to stand for 30 minutes to yield taffy-like precipitate at the bottom of beaker but not a highly fluid homogeneous suspension.

COMPARATIVE EXAMPLE 7

The same procedure as in Example 9 was repeated except for adding 1.6 g of agar (DIFCO) to about 400 ml of an extract of Hydrangeae Dulcis Folium, in stead of adding 1.6 g of Hydrangeae Dulcis Folium powder, and 60 ml of concentrate was obtained. The obtained concentrate was put in to a 100 ml-beaker and allowed to stand for 30 minutes to yield taffy-like precipitate at the bottom of beaker but not a highly fluid homogeneous suspension.

COMPARATIVE EXAMPLE 8

The same procedure as in Example 9 was repeated except for adding 1.6 g of starch (Nippon Starch Chemical Co.) to about 400 ml of an extract of Hydrangeae Dulcis Folium, in stead of adding 1.6 g of Hydrangeae Dulcis Folium powder, and 60 ml of concentrate was obtained. The obtained concentrate was put into a 100 ml-beaker and allowed to stand for 30 minutes to yield taffy-like precipitate at the bottom of beaker but not a highly fluid homogeneous suspension.

COMPARATIVE EXAMPLE 9

The same procedure as in Example 9 was repeated except for adding 1.6 g of Pinedex #1 (Matsutani Chemical Industry Co., Ltd.) to about 400 ml of an extract of Hydrangeae Dulcis Folium, in stead of adding 1.6 g of Hydrangeae Dulcis Folium powder, and 60 ml of concentrate was obtained. The obtained concentrate was put into a 100 ml-beaker and allowed to stand for 30 minutes to yield taffy-like precipitate at the bottom of beaker but not a highly fluid homogeneous suspension.

COMPARATIVE EXAMPLE 10

The same procedure as in Example 9 was repeated excepted for adding 1.6 g of gum arabic (Kishida Chemical Co., Ltd.) to about 400 ml of an extract of Hydrangeae Dulcis Folium, in stead of adding 1.6 g of Hydrangeae Dulcis Folium powder, and 60 ml of concentrate was obtained. The obtained concentrate was put into a 100 ml-beaker and allowed to stand for 30 minutes to yield taffy-like precipitate at the bottom of beaker but not a highly fluid homogeneous suspension.

COMPARATIVE EXAMPLE 11

The same procedure as in Example 9 was repeated excepted for adding 1.6 g of lactose (Kishida Chemical Co., Ltd.) to about 400 ml of an extract of Hydrangeae Dulcis Folium, in stead of adding 1.6 g of Hydrangeae Dulcis Folium powder, and 60 ml of concentrate was obtained. The obtained concentrate was put into a 100 ml-beaker and allowed to stand for 30 minutes to yield taffy-like precipitate at the bottom of beaker but not a highly fluid homogeneous suspension.

INDUSTRIAL APPLICABILITY

According to the present invention, a process for extracting an active ingredient from a plant containing the active ingredient, a liquid extract or plant extract containing the active ingredient, and a food and drink or feed containing the liquid extract or plant extract, are provided.

The invention claimed is:

1. A process for producing an extract of *Hydrangea*, which comprises the steps of:
    obtaining a liquid extract of *Hydrangea*;
    admixing a plant powder with said liquid extract; and
    concentrating said admixed powder and liquid extract by heating under reduced pressure only.

2. A process for producing an extract of *Hydrangea*, which comprises the steps of:
    obtaining a liquid extract of *Hydrangea*;
    obtaining a plant powder;
    admixing said plant powder with said liquid extract; and
    concentrating said admixed powder and liquid extract by heating under reduced pressure only.

3. A process for producing an extract of *Hydrangea*, which comprises the steps of:
    obtaining a liquid extract of *Hydrangea*;
    obtaining a plant powder;
    admixing said powder with said liquid extract;
    concentrating said admixed powder and liquid extract by heating under reduced pressure only; and
    drying said concentrated mixture of powder and liquid extract.

4. A process as claimed in any of claims 1 to 3, wherein the liquid extract is prepared by extracting *Hydrangea* with aqueous ethanol and removing the resultant residue.

5. A process as claimed in any of claims 1 to 3, wherein the powder is present in an amount of 19 to $1/19$ parts by dry weight based on 1 part of the liquid extract by weight.

6. A process as claimed in claim 5, wherein the *Hydrangea* is *Hydrangea macrophylla* SERINGE var. *Thunbergii Makino*.

7. A process as claimed in claim 6, wherein the extract contains phyllodulcin.

8. A process as claimed in claim 5, wherein the powder is in the form of particles of 0.1 mm to 1 mm in average particle size in dry state.

9. A process as claimed in claim 8, wherein the powder is *Hydrangea* powder.

10. A process as claimed in claim 8, wherein the powder is *Hydrangeae* Dulcis Folium powder, green tea powder or turmeric powder.

11. A process as claimed in claim 4, wherein the powder is present in an amount of 19 to $1/19$ parts by dry weight based on 1 part of the liquid extract by weight.

12. A process as claimed in claim 11, wherein *Hydrangea* is *Hydrangea macrophylla* SERINGE var. *Thunbergii Makino*.

13. A process as claimed in claim 12, wherein the extract contains phyllodulcin.

14. A process as claimed in claim 11, wherein the powder is in the form of particles of 0.1 mm to 1 mm in average particle size in dry state.

15. A process as claimed in claim 14, wherein the powder is *Hydrangea* powder.

16. A process as claimed in claim 14, wherein the powder is *Hydrangeae* Dulcis Folium powder, green tea powder or turmeric powder.

* * * * *